(12) United States Patent
Patrício Domingues Gonçalves et al.

(10) Patent No.: US 11,933,654 B2
(45) Date of Patent: Mar. 19, 2024

(54) LEVEL AND/OR DENSITY SENSOR DEVICE FOR LIQUID VESSELS

(71) Applicant: Watgrid, Lda., Ílhavo (PT)

(72) Inventors: Fábio Patrício Domingues Gonçalves, Santiago de Litém (PT); Lúcia Maria Botas Bilro, Gafanha Da Encarnação (PT); Rogério Nunes Nogueira, Beira Litoral (PT)

(73) Assignee: Watgrid, S.A. (PT)

( * ) Notice: Subject to any disclaimer, the term of this patent is extended or adjusted under 35 U.S.C. 154(b) by 34 days.

(21) Appl. No.: 16/207,514

(22) PCT Filed: Jun. 14, 2017

(86) PCT No.: PCT/IB2017/053549
§ 371 (c)(1),
(2) Date: Dec. 3, 2018

(87) PCT Pub. No.: WO2017/216746
PCT Pub. Date: Dec. 21, 2017

(65) Prior Publication Data
US 2019/0185806 A1    Jun. 20, 2019

(30) Foreign Application Priority Data
Jun. 14, 2016    (PT) .......................... 109451

(51) Int. Cl.
*G01F 23/14*    (2006.01)
*G01F 23/16*    (2006.01)
(Continued)

(52) U.S. Cl.
CPC ............ *G01F 23/14* (2013.01); *G01F 23/168* (2013.01); *G01F 23/18* (2013.01); *G01N 9/26* (2013.01); *C12M 41/44* (2013.01)

(58) Field of Classification Search
CPC .. G01F 23/14–185; G01N 9/26; G01N 9/266; G01N 2009/263
See application file for complete search history.

(56) References Cited

U.S. PATENT DOCUMENTS 4,455,876 A  *  6/1984  McPherson ............... G01L 7/18
73/747
4,669,309 A  *  6/1987  Cornelius ............... G01F 23/14
73/299

(Continued)

FOREIGN PATENT DOCUMENTS

DE          20110719 U1    9/2001
EP          1270716 A1     1/2003
(Continued)

OTHER PUBLICATIONS

Int'l Search Report and Written Opinion Appln No. PCT/IB2017/053549 dated Sep. 26, 2017.

(Continued)

*Primary Examiner* — Justin N Olamit
(74) *Attorney, Agent, or Firm* — McAndrews, Held & Malloy, Ltd.

(57) ABSTRACT

The present disclosure is related to a level and/or density sensor for vessels suitable for storing liquids, in particular barrels or vats, more in particular barrels or vats for storing or producing wine. The hydrostatic pressure differential sensor for measuring volume and/or density disclosed herein comprises a main body; a tube for diving into the liquid; a hydrostatic pressure differential sensor; an air injector for injecting air into said tube; wherein the tube is coupled to the main body; wherein the hydrostatic pressure differential sensor has two inlets, a first inlet airtight connected to the upper top of said tube, configured so that the tube maintains air present in the interior thereof when dived into the liquid, (Continued)

and a second inlet for communicating with the interior of the vessel.

25 Claims, 8 Drawing Sheets

(51) Int. Cl.
    *G01F 23/18*      (2006.01)
    *G01N 9/26*      (2006.01)
    *C12M 1/34*      (2006.01)

(56) References Cited

U.S. PATENT DOCUMENTS

| | | | |
|---|---|---|---|
| 4,984,451 A | | 1/1991 | Wilen et al. |
| 5,115,679 A | * | 5/1992 | Uhlarik .................... G01N 9/28 73/302 |
| 5,146,783 A | * | 9/1992 | Jansche ................ G01F 23/168 73/301 |
| 5,163,324 A | * | 11/1992 | Stewart ................ G01F 23/168 73/301 |
| 5,423,226 A | * | 6/1995 | Hunter .................... G01F 1/363 73/215 |
| 5,587,527 A | | 12/1996 | Radford et al. |
| 5,953,954 A | * | 9/1999 | Drain ....................... G01N 9/28 73/301 |
| 6,826,956 B1 | * | 12/2004 | Mathews ............... G01F 23/165 73/290 R |
| 7,140,404 B2 | * | 11/2006 | Cupples ................ G01F 23/164 141/95 |
| 7,251,998 B2 | * | 8/2007 | Gourlay .................. G01F 23/14 73/290 R |
| 2004/0076946 A1 | | 4/2004 | Trauner |
| 2015/0198474 A1 | * | 7/2015 | Howard .................... C12G 1/00 702/55 |
| 2018/0319587 A1 | * | 11/2018 | Aston ................ B65D 77/0466 |

FOREIGN PATENT DOCUMENTS

| | | |
|---|---|---|
| FR | 2639710 A1 | 6/1990 |
| FR | 2641865 A1 | 7/1990 |
| WO | 2017216746 A1 | 12/2017 |

OTHER PUBLICATIONS

Australian Examination Report Appln No. 2017283809 dated May 31, 2021.
Australian Examination Report Appln No. 2017283809 dated Jan. 14, 2022.
Australian Examination Report Appln No. 2017283809 dated May 12, 2022.
Australian Examination Report No. 1 Appln No. 2022203783 dated May 24, 2023.

* cited by examiner

LEVEL AND/OR DENSITY SENSOR DEVICE FOR LIQUID VESSELS

CROSS-REFERENCE TO RELATED APPLICATIONS

The present application is a 35 U.S.C. § 371 filing and continuation of application Serial No. PCT/IB2017/053549, filed on Jun. 14, 2017, and entitled "LEVEL AND/OR DENSITY SENSOR DEVICE FOR LIQUID RECEPTACLES." The aforementioned application is hereby incorporated herein by reference in its entirety.

TECHNICAL FIELD

The present disclosure is related to a level and density sensor device for vessels suitable for storing liquids, in particular barrels or vats, more in particular barrels or vats for storing or producing wine.

BACKGROUND

The wine-making process is a set of technical operations allowing the transformation of grapes into wine and comprising several steps among which wine fermentation, ageing and storage steps in barrels/tuns/casks/vats or other vessels suitable for the purpose.

Offline control by sampling means is the most common form of controlling the wine-making process, namely for controlling the density.

The control of the wine level, when stored in barrels, normally implies opening the barrel, removing the stopper, for verifying the existing space between the top of the barrel and the liquid level.

Controlling the level is essential for ullage, which consists of resetting the level for compensating the losses occurred through gaseous exchange, which usually occurs every 2/3 months. It is estimated that each barrel loses 7 to 11 litres of wine, depending on the environmental conditions.

Gaseous exchanges are directly related to the wine oxygen dissolution, with various redox reactions occurring, which will form unstable compounds, leading to changes in colour and wine astringency and contributing to the ethanol oxidation to acetaldehyde, being that the acetaldehyde contributes afterwards to the copolymerisation of the flavonoids and anthocyanins.

The existence of an excessive air pocket promotes wine oxidation. Therefore, the wine level control is related to the quantity of available oxygen.

In the alcoholic fermentation step (transformation of sugars into alcohol) measuring the liquid density (must) is one of the ways of controlling the activity of yeasts, allowing for accompanying the fermentation progress.

These facts are described so as to illustrate the technical problem solved by the embodiments of this document.

GENERAL DESCRIPTION

The present disclosure is related to a level and/or density sensor device for vessels suitable for storing liquids, in particular barrels or vats, more in particular barrels or vats for fermenting, storing and producing wine.

Offline control by sampling means is the most common way of controlling the wine-making process. However, this way of control, by sampling, translates into a process that:
  must be carried out by an operator on the wine storage location;
  consumes time and resources for wine producers, since it is a manual process;
  induces an action/reaction cycle causing greater variations, which leads to a lower wine quality;
  is carried out only for a fraction of the production and consequently, the product quality is not uniform.

The importance of knowing at every moment what is the level and density of the liquid contained in a cask/tun/barrel/vat, relates to the following aspects:

| Variable of interest | Barrel | Fermentation and/or storage reservoir |
| --- | --- | --- |
| Level | Wine - At the ageing stage it allows accompanying the evaporation, which is directly related to the gaseous exchanges with the exterior, allowing for evaluating the need to carry out ullage. Spirit drinks - At the ageing stage it allows accompanying the evaporation, which is directly related to the alcohol content of the spirit drink. | It may detect the existence of leakage, unusual liquid evaporation and stock control. |
| Density | Wine - It allows accompanying it in the fermentation stage, that is, the sugar degradation, being that the yeast activity is followed so as to transform sugar into alcohol (in the fermentation stage density may go from 1100 kg/m$^3$ to 990 kg/m$^3$ at a temperature of 20° C.). Spirit drinks - In the ageing stage it allows accompanying the reduction of the alcohol content. | Wine - It allows accompanying it in the fermentation stage, that is, the sugar degradation. |

Controlling the level and density of the liquid contained in a cask/tun/barrel/vat is a complex and lengthy process for being carried out manually, considering, for example, that each barrel vat may contain a different liquid, or be in a fermentation/ageing stage different than the remaining barrels/vats, that is, there may exist a plurality of different needs for the various barrels/vats. Therefore, this problem is solved with the present disclosure through the implementation of the sensor device disclosed herein in each barrel vat.

Solutions currently existing in the market present the following limitations: don't allow for an automated/in real time monitoring (buoy solution); present a high cost reducing economic viability; are affected by the deposition of sediments/particles (crystallisation effects), needing a regular maintenance (capacitive/pressure sensors with membranes in direct contact with the liquid); operation ranges outside the necessary requirements (ultrasounds distances>300 mm) and insufficient resolutions (>1 mm ultrasounds).

The advantages of the present disclosure comprise:
  increasing the wine quality;
  reducing waste, since the sampling need for chemical analyses and additionally losses from meagre monitoring of the quality, possibly leading to the total loss of the product;
  reducing control costs;
  possibility of controlling a set of barrels through a network of sensor devices incorporated in a monitoring platform, which translates into control and monitoring in real time;
  the physical and chemical integrity of the liquid is not endangered (there is no contamination);
  facilitating the maintenance since the particle deposition does not compromise the functioning of the sensor device.

In an embodiment, it is possible to control the following parameters in real time: level, density, temperature, pH, turbidity, colour, sugar and alcohol quantity contained in the vessel/barrel/tun/cask/vat, namely through the use of additional sensors.

Embodiments of the present disclosure comprise the possibility of controlling the various parameters aforementioned more than once; sending notifications when the monitored parameters are outside the limits defined by the user; real time monitoring; wireless communication; detecting anomalies, detecting typical profiles, comparing history data, data mining, big data algorithms, anticipating/forecasting maintenance tasks, production management, increasing energy efficiency.

The present disclosure allows measuring the hydrostatic pressure of a liquid contained, for example, in a barrel without having to open it, since the variation of the hydrostatic pressure between two points, one situated on the free surface of the liquid and another situated in the point from which the measurement is intended to be carried out (level measurement). Therefore, avoiding opening the barrel also translates into the following advantages: avoiding excessive gaseous exchanges leading to the excessive dissolution of oxygen leading to the formation of compounds, resulting from redox reactions, increasing the risk of loss of the quality potential or even the total loss of the product.

The present disclosure is related to the hydrostatic pressure, that is, it is related to the forces exerted by and on fluids at rest and relates to a level or density sensor device for barrels/sensorised stopper for barrels or vats, in particular a differential pressure sensor allowing for determining the level of a liquid contained in a vessel suitable for storing liquids, in particular, wine and also allowing for determining the density of said liquid contained in the vessel/barrel.

The hydrostatic pressure is determined by Stevin's theorem. The operating principle of the level measurement by the sensorised stopper is based on Stevin's theorem: $P = \rho g h$ wherein P corresponds to the hydrostatic pressure created by a column of liquid, $\rho$ corresponds to the density of the liquid in $kg/m^3$, g corresponds to the gravity acceleration in $m/s^2$, h corresponds to the liquid height/level above the measure point in metres. By measuring the value of P and considering that the value of $\rho$ and g are constant after the calibration has been made, it is possible to obtain the value of k which in this case represents the level of the liquid inside the barrel.

Figure 1:
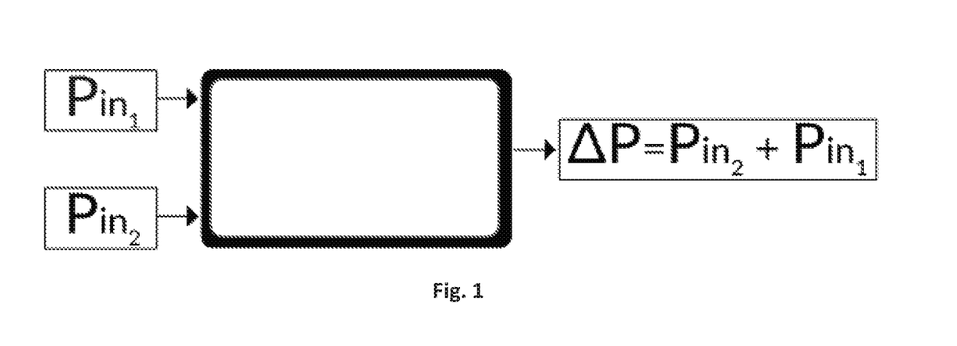
FIG. 1: Schematic representation of the operation of the differential sensor device used.

In order to obtain the value of the differential hydrostatic pressure in the liquid ($\Delta P$) a differential pressure sensor is used, which measures the air or liquid pressure (FIG. 1).

Considering a point in the top of the barrel (in the air pocket) and another in the end of a tube dived into the liquid, the hydrostatic pressure is transmitted to the sensor through air that stays "captured" inside the tight tubes connected to the differential pressure sensor. Therefore, the differential pressure sensor compares the pressure between the air pressure inside the barrel and the air pressure in the tube end, with possibility of the differential pressure sensor being situated at the top of the barrel, namely integrated in a stopper, which simplifies the device construction and operation, namely sparing two sensors.

The equation necessary for measuring the density, in the particular case of using two tubes with a $\Delta h$, is said Stevin's theorem. If the values of g and $\Delta h$ are deemed constant and the value of $\Delta P$ is measured, it is possible to obtain the value of $\rho$, which in this case is the value of the liquid density.

The compensation of temperature causing the pressure of the air pocket to vary applies to both sides of the difference.

In an embodiment, if there is temperature variation inside the barrel, the air "captured" inside the measurement tubes expands, as a result of the temperature increase, or in opposition it contracts in case the temperature decreases. This leads to a variation of the hydrostatic pressure without a variation of the level, giving rise to a reading error.

This fact makes it necessary to acquire the temperature and compensate it for making the level measurement immune to that variation of the pressure inside the measurement tube.

In an embodiment, the "meniscus" effect is described and avoided, namely the weight thereof in the exact determination of the density, as well as other effects (dissolved gas). If the liquid inside the vessel releases gas (phenomenon occurring during the fermentation, resulting from the activity of yeasts), it may accumulate in the ends of the tube or tubes in case 2 tubes are dived in. The "meniscus" effect leads to the appearance of a "bubble" in the lower end of the measurement tube which releases itself whenever it has sufficient size for that to happen. This situation translates into a variation of the hydrostatic pressure without a variation of the level of the liquid or density thereof, thereby introducing a reading error. The bigger the "bubble" that can be accumulated by the "meniscus" effect, the bigger the introduced error. For minimising this error, the end of the tubes must have such a shape that it minimises the "meniscus" effect.

The present disclosure relates to a sensor device that may have the simultaneous function of vessel stopper or other format convenient to the installation, for measuring through a hydrostatic pressure difference, the volume or the density of a liquid contained in the vessel, wherein said sensor device comprises:
  a main body;
  a tube coupled to the main body for diving into the liquid when the vessel is covered or not with the sensor device;
  a hydrostatic pressure differential sensor placed in the main body;
  wherein the hydrostatic pressure differential sensor has two sensor inlets, a first inlet tight connected to the upper top of said tube so that the tube maintains air present in the interior thereof when dived into the liquid, and a second inlet for communicating with the interior of the vessel.

The present disclosure also relates to a sensor device of hydrostatic pressure difference for measuring volume or density of a liquid contained in a vessel, wherein said sensor device comprises:
  a main body;
  a tube for diving into the liquid;
  a hydrostatic pressure differential sensor;
  an air injector for injecting air into said tube;
  wherein the tube is coupled to the main body;
  wherein the hydrostatic pressure differential sensor has two inlets, a first inlet airtight connected to the upper top of said tube, configured so that the tube maintains air present in the interior thereof when dived into the liquid, and a second inlet for communicating with the interior of the vessel.

In an embodiment, it is foreseen the introduction of air into the measurement tubes (tube(s) for diving into the liquid), being that such air may be introduced through one or more air injectors, such as for example: air pumps, bottles with compressed air or any other pressurisation form.

The air injector allows for the air column and meniscus thereof to be reconstructed in a given measurement tube, before carrying out measure, for expelling the liquid that has introduced in the interior of the tube throughout time (for example, due to air leakages in the tube or in the pressure sensor); it also allows for expelling air from the tubes whenever necessary for removing any dirt, that has introduced in the tubes, through air injection.

In an embodiment, the sensor device may measure, through a hydrostatic pressure difference, the density of the liquid contained in the vessel wherein said sensor device may comprise:
- a second tube coupled to the main body for diving into the liquid, being that the length of the second tube is different from the length of the first tube and
- wherein the second inlet of the hydrostatic pressure differential sensor is airtight connected to the upper top of the second tube so that the second tube maintains air present in the interior thereof when dived into the liquid.

In an embodiment, the sensor device may measure the volume and density of the liquid contained in the vessel, being that the sensor device may comprise:
- a second tube coupled to the main body for diving into the liquid, being that the length of the second tube is different from the length of the first tube and
- a second hydrostatic pressure differential sensor;
- wherein the second hydrostatic pressure differential sensor may have two inlets, a first inlet of the second differential sensor airtight connected to the upper top of the first tube, configured so that the tube maintains air present in the interior thereof when dived into the liquid, and a second inlet of the second differential sensor tight connected to the upper top of the second tube so that the second tube maintains air present in the interior thereof when dived into the liquid.

In an embodiment, the first or the second differential hydrostatic pressure differential sensor may comprise two non-differential pressure sensors and a differentiator for providing the difference between the pressures measured by the two non-differential sensors.

In an embodiment, the sensor device disclosed herein may comprise an additional tube for protecting the second inlet of the first hydrostatic pressure differential sensor.

In an embodiment, one or more of each tube, in particular of all the tubes, has an air injector for injecting air into the corresponding tube.

In an embodiment, the sensor device herein disclosed may comprise an electronic data processor connected to the hydrostatic pressure differential sensor and to the air injector, wherein said processor is configured for injecting air into said tube before obtaining a measure by the hydrostatic pressure differential sensor, in particular said processor is configured for injecting air into said tube immediately before obtaining a measure by the hydrostatic pressure differential sensor.

In an embodiment, the tube or tubes may have an inferior end angle-cut for avoiding or minimising meniscus effect of the liquid in the inferior end of the tube or tubes, in particular the inferior end may be angle-cut of 30-60°, preferably 45°.

In an embodiment, the tube or tubes may have an inferior end angle-cut for avoiding or minimising meniscus effect of the liquid in the inferior end of the tube or tubes.

In an embodiment, one or more tubes may have a superior end angle-coupled to the main body for avoiding or minimising the meniscus effect of the liquid in the inferior end of the tube or tubes.

In an embodiment, the tube or tubes may be stainless, teflon or plastic tube or tubes.

In an embodiment, the sensor device may comprise a temperature sensor coupled to the main body or to a said tube.

In an embodiment, the sensor device may comprise a sensor for measuring pH, turbidity, colour, sugar amounts or alcohol concentration of the liquid, or combinations thereof, coupled to the main body or to a said tube.

In an embodiment, the sensor device may be cylindrical, quadrangular section prismatic, rectangular section prismatic, or frusta-conical.

In an embodiment, the sensor device may comprise a wireless transmitter for transmitting data collected by the sensor or sensors of pH, turbidity, colour, sugar amounts or alcohol concentration of the liquid, or combinations thereof, coupled to the main body or to a said tube, being that the collected data may be transmitted periodically.

In an embodiment, the liquid may be wine, sparkling wine, juice, or a spirit drink.

In an embodiment, the vessel may be a barrel, tun, cask or vat.

In an embodiment, the sensor device herein disclosed may be a stopper of a said vessel, for example wherein the vessel may be a barrel, tun, cask or vat.

The present disclosure also relates to a barrel, a tun, a cask or vat that may comprise the sensor device disclosed herein.

The present disclosure further relates to a system for measuring volume and density of a liquid contained in vessels comprising a plurality of sensor devices herein disclosed.

In an embodiment, said system may comprise a data electronic processor that may be configured for receiving, processing and storing the data collected by the sensor device.

In an embodiment, said processor may generate and send an alert for at least a user via email or SMS.

Throughout the description and claims the word "comprises" and variations of the word "comprises", are not intended to exclude other technical features, as other components or steps. Additional objects, advantages and features of the disclosure will become clear to those skilled in the art upon examination of the description or may be learned by practice of the invention. The following examples and figures are for illustrating the description and should not be seen as limiting the scope of the disclosure. Furthermore, the present disclosure covers all possible combinations of specific or preferential embodiments herein described.

BRIEF DESCRIPTION OF THE DRAWINGS

For an easier understanding of the present disclosure figures are attached, which, represent preferred embodiments for illustrating the description and should not be seen as limiting the scope of the disclosure.

DETAILED DESCRIPTION

Figure 2:
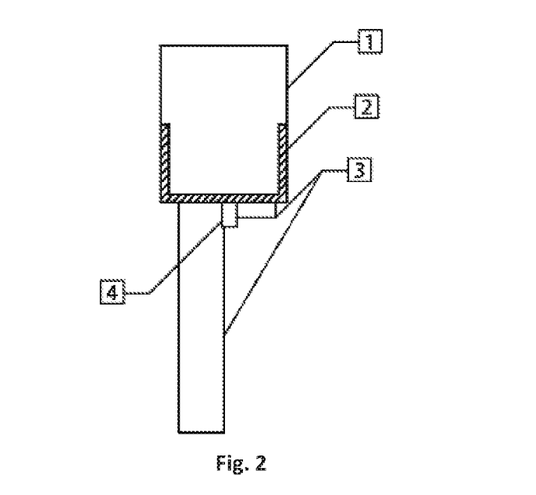
FIG. 2: Side view schematic representation of the set for measuring the level.

FIG. 2 represents an embodiment for measuring the level of the liquid contained in the barrel, disclosing some of the components comprised in the present disclosure. FIG. 2 represents in particular a side view of the present disclosure wherein 1 represents the carcass main body of the stopper/sensor device, 2 represents a silicone joint, that may exist or not, on accumulating stopper function (tightness) or not of the vessel; 3 represents two tubes connected to the sensor, one for measuring the air pocket pressure and another with air in the interior thereof for measuring the liquid pressure at a given depth, in particular tubes that may comprise in the composition thereof a material compatible with the liquid with which stainless steel, teflon or plastic is in contact; and 4 represents a temperature sensor.

Figure 3:
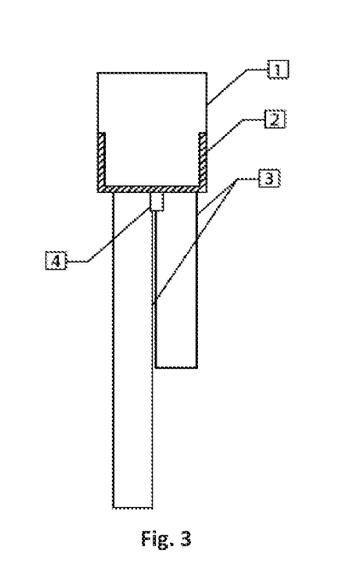
FIG. 3: Side view schematic representation of the set for measuring the density.

FIG. 3 represents an embodiment, in particular it represents a side view of the set disclosed herein for measuring the liquid density contained in the barrel, with two tubes connected to the sensor with air in the interior thereof for measuring the liquid pressure at two predetermined depths.

Figure 4:
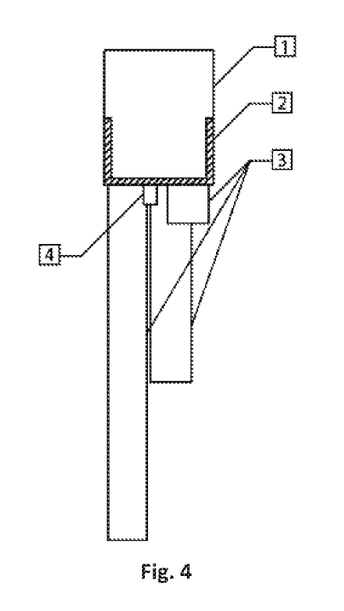
FIG. 4: Side view schematic representation of the set for measuring the level and density.

FIG. 4 represents an embodiment of the present disclosure, in particular it represents a side view of the set for measuring the liquid level and density contained in the barrel, with three tubes connected to the sensor, one for measuring the air pocket pressure and two tubes with air in the interior thereof for measuring the liquid pressure at two predetermined depths.

The tube for measuring the pressure in the air pocket in the described embodiments is optional, since the sensor will function equally well without it. The tube has here a physical protection function of the sensor.

The temperature sensor is optional, in case the temperature measure is not used or is provided by another sensor, inside or outside the barrel.

Figure 5:
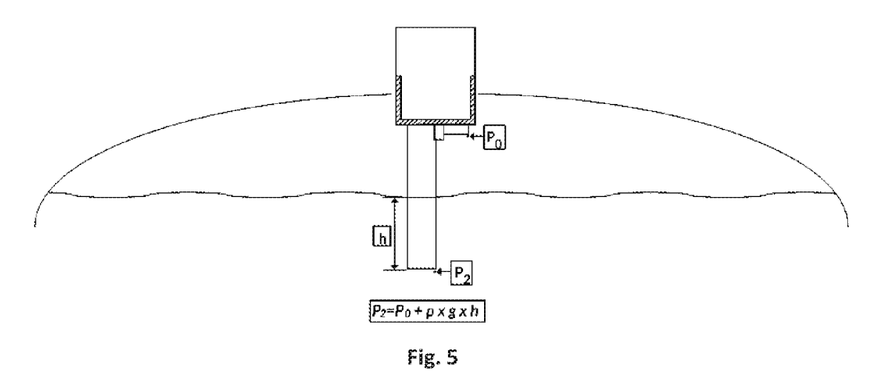
FIG. 5: Side view schematic representation of the set for measuring the level placed in the barrel.

FIG. 5 represents an architecture of the monitoring platform, in particular a side view of the measurement set in the level placed in the barrel, being that $P_0$ represents the hydrostatic pressure measured in the interior of the vessel; $P_2$ represents the hydrostatic pressure measured in the tube end (first tube) that is dived into the liquid contained in the barrel and h represents the height between the point where the measurement of $P_2$ is made and the surface of the liquid.

Figure 6:
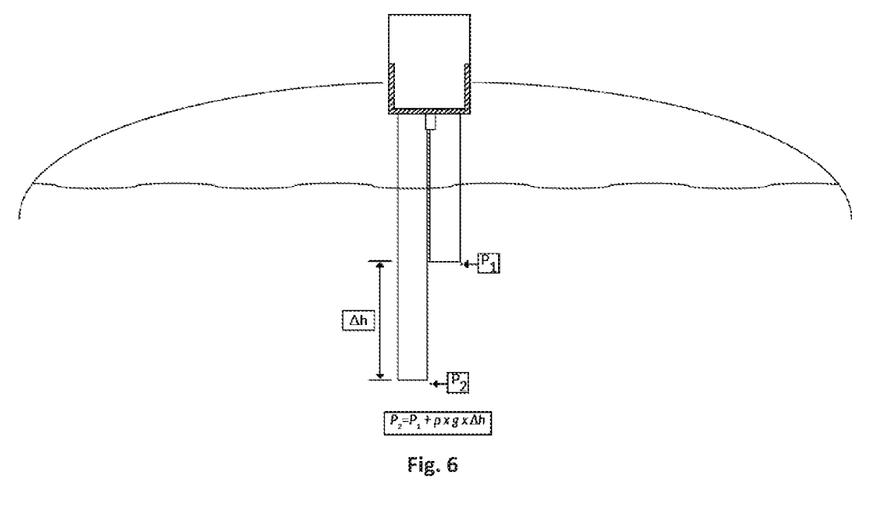
FIG. 6: Side view schematic representation of the set for measuring the density placed in the barrel.
Figure 7:
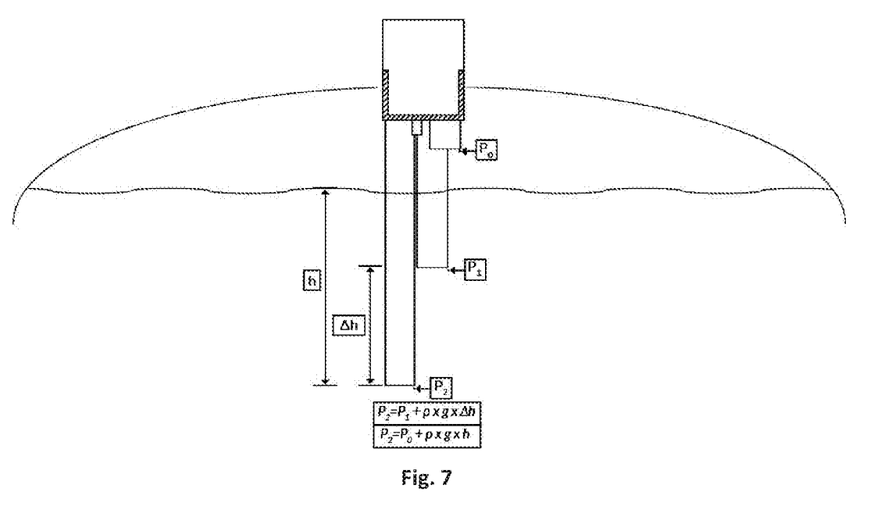
FIG. 7: Side view schematic representation of the set for measuring the level and density placed in the barrel.
Figure 8:
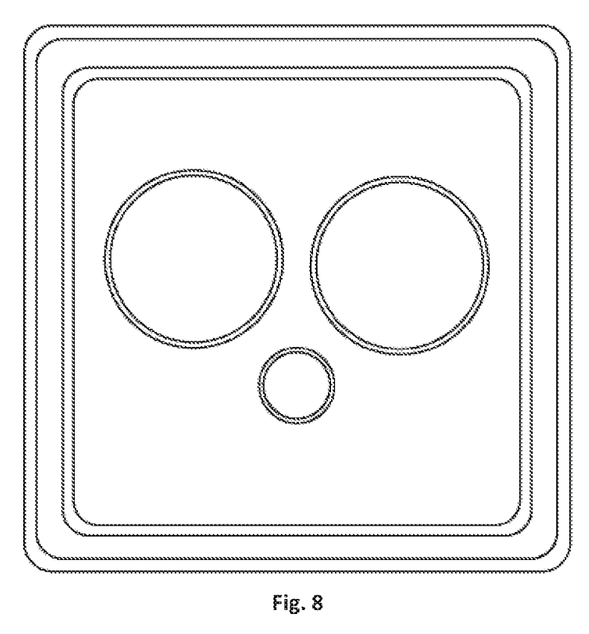
FIG. 8: Bottom view schematic representation of the set for measuring the level or density.
Figure 9:
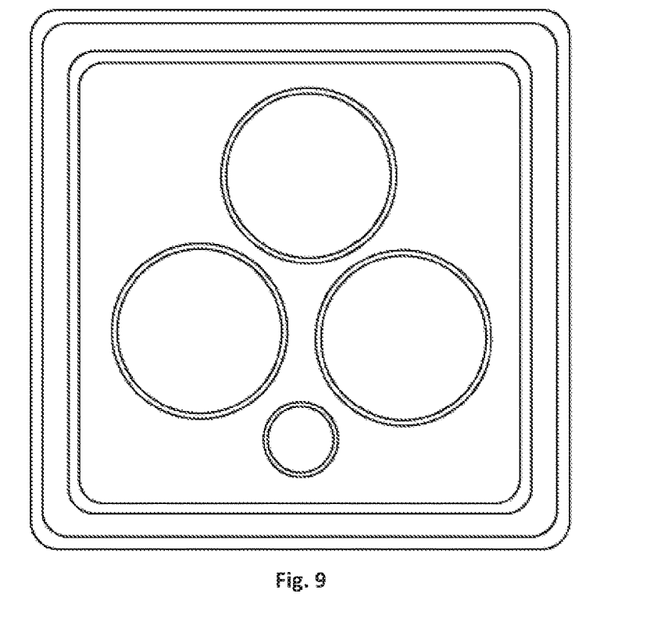
FIG. 9: Bottom view schematic representation of the set for measuring the level and density.
Figure 10:
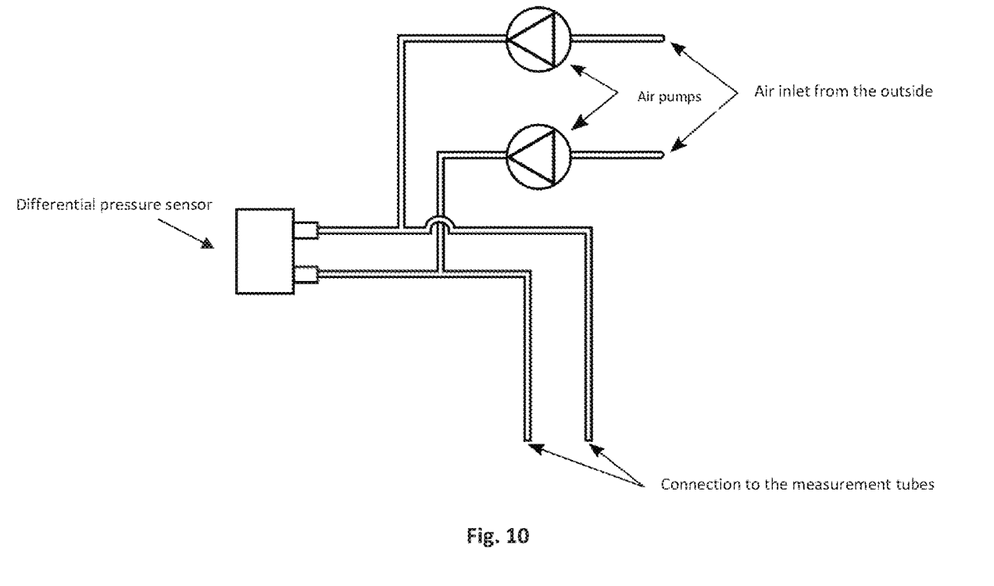
FIG. 10: Schematic representation of the system with pumps for introducing air or air injectors.
Figure 11:
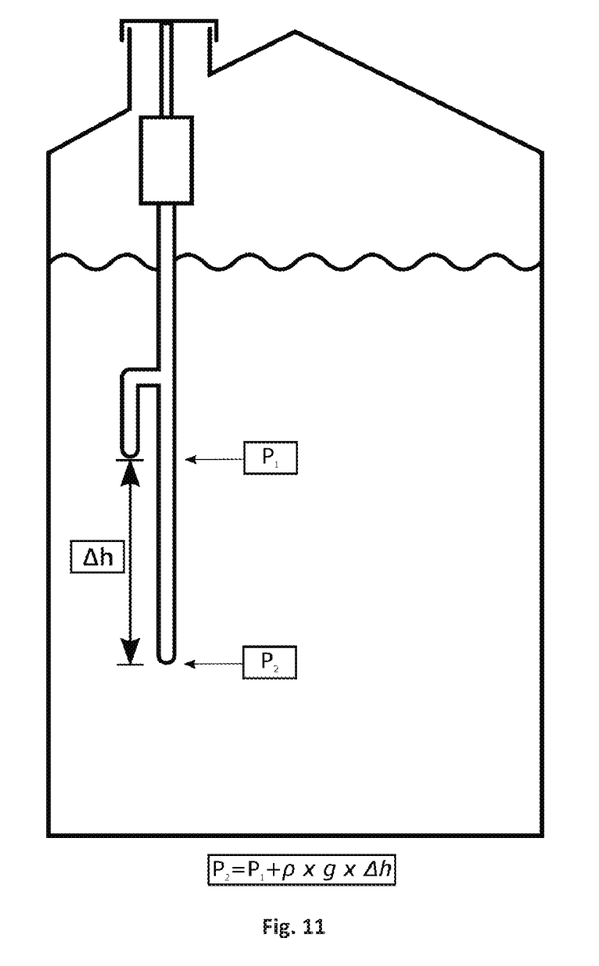
FIG. 11: Side view schematic representation of the set for measuring the density placed in the vat.

FIG. 6 represents the architecture of the monitoring platform in particular a side view of the set for density measurement placed in the barrel wherein $P_2$ represents the hydrostatic pressure measured in the tube end (first tube) that is dived into the liquid contained in the barrel, $P_1$ represents the hydrostatic pressure measured in the end of a second tube that is dived into the liquid contained in the barrel and $\Delta h$ represents the height difference between the points $P_1$ and $P_2$. FIG. 6 represents a joint embodiment of the level and density sensor.

Figure 12A:
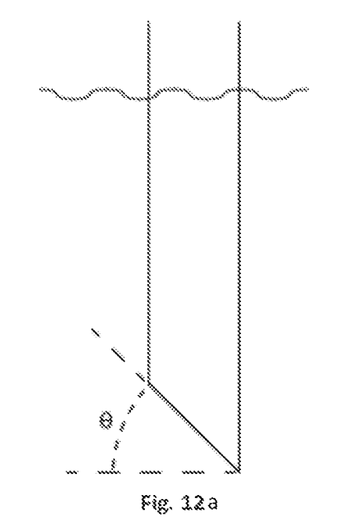
FIGS. 12*a-c*: Schematic representation of the embodiment for preventing the "meniscus" effect by the angle-cut of the inferior end of the measurement tube.
Figure 12B:
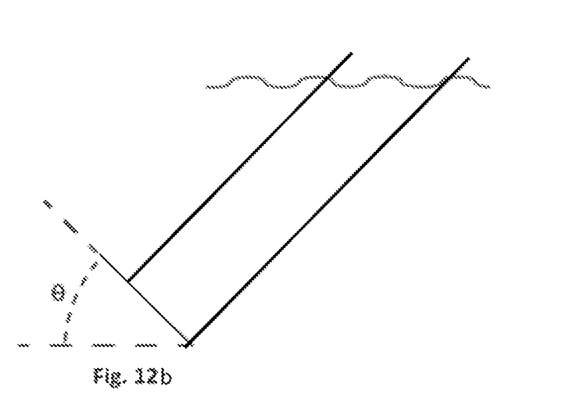
Figure 12C:
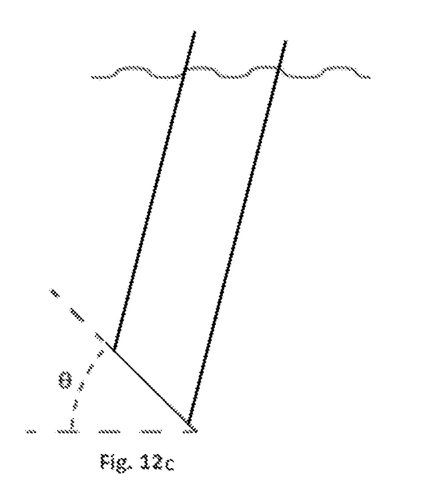
Figure 13:
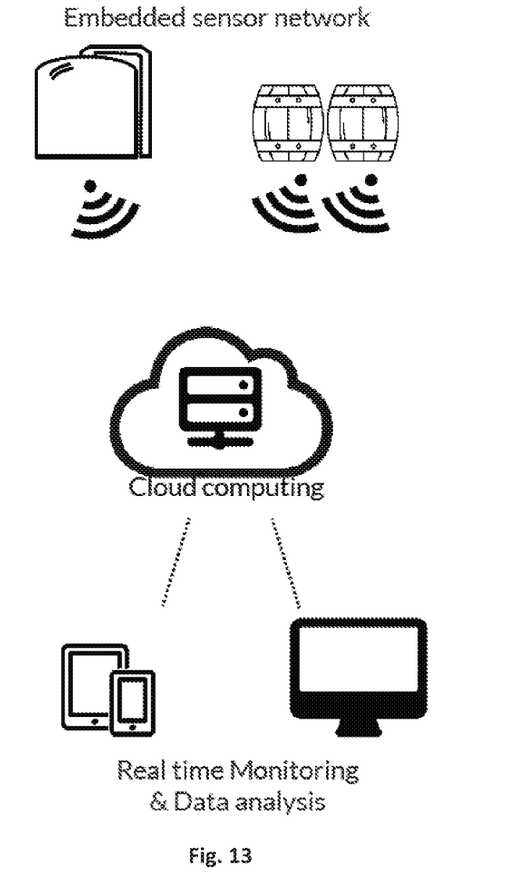
FIG. 13: Schematic representation of the integrated system herein disclosed.

FIG. 12*a* represents an embodiment allowing for reducing or minimising the meniscus effect that may introduce reading errors, either of liquid level or density level. Therefore for avoiding or minimising the meniscus effect, each tube may comprise in the inferior end thereof an angle-cut, for example between 30-60°, preferably 45°, being that this angle is measured between the inferior opening plan of the tube and the liquid surface. Alternatively (as illustrated in FIG. 12*b*) or complementarily (as illustrated in FIG. 12*c*), the tube may be tilted in relation to the vertical.

In an embodiment, the initial calibration may be carried out by the following steps:
carrying out a measure with the sensor outside the liquid, that is in the air; carrying out a measure with the sensor dived into the liquid d/2 mm (where d represents the total length of the sensor in mm, that is, it represents the maximum value of the level the sensor can measure);
carrying out a measure with the sensor dived into the liquid d mm (where d represents the maximum value of the level the sensor can measure).

In an embodiment, the initial calibration may also be carried out by the following steps:
carrying out a measure with the sensor outside the liquid, that is in the air; carrying out a measure with the sensor dived into the liquid d/3 mm (where d represents the maximum value of the level the sensor can measure);
carrying out a measure with the sensor dived into the liquid 2×d/3 mm (where d represents the maximum value of the level the sensor can measure);
carrying out a measure with the sensor dived into the liquid d mm (where d represents the maximum value of the level the sensor can measure).

In an embodiment, the initial calibration carried out in 4 steps is a more precise calibration than the calibration carried out in 3 steps because more points are obtained giving rise to a better adjustment equation, decreasing the error associated to the calibration.

Although merely particular embodiments of the present disclosure have been represented and described herein, those skilled in the art will know how to introduce modifications and replace some technical features with equivalent ones, depending on the requisites of each situation, without departing from the scope of protection defined by the appended claims. The term "comprises" or "comprising" when used in this document is intended to indicate the presence of the mentioned features, elements, integers, steps and components, but not to preclude the presence or addition of one or more other features, integers, steps and components or combinations thereof. The following claims additionally set out embodiments of the disclosure.

The invention claimed is:

1. A sensor device, wherein the sensor device comprises:
a main body;
a first stainless steel tube comprising two ends, and wherein:
the first stainless steel tube has a first end that is coupled to the main body,
the first stainless steel tube is configured to be submerged in a liquid contained in a vessel,
the first stainless steel tube is tilted in relation to vertical to form an angle as measured between an opening at a second end of the first stainless steel tube and a surface of the liquid, wherein the first stainless steel tube is straight between the first end to the second end and configured to be both submerged in the liquid and tilted in relation to vertical; and
the angle is greater than 30° and less than 60°;

a first air injector, within the main body, for injecting air into the first end of the first stainless steel tube; and a first hydrostatic pressure differential sensor, within the main body, configured to collect data to measure a volume of the liquid contained in the vessel according to pressures at two inlets of the first hydrostatic pressure differential sensor, wherein a first inlet of the first hydrostatic pressure differential sensor is operably coupled to the first end of the first stainless steel tube, and wherein a second inlet of the first hydrostatic pressure differential sensor is configured to communicate with an interior of the vessel, and wherein the first hydrostatic pressure differential sensor is configured to maintain air in the first stainless steel tube when the second end of the first stainless steel tube is inserted into the liquid contained in the vessel.

2. The sensor device of claim 1, wherein the sensor device comprises:
a second stainless steel tube comprising two ends, wherein a length of the second stainless steel tube is different from a length of the first stainless steel tube, and wherein the second inlet of the first hydrostatic pressure differential sensor is operably coupled to a first end of the second stainless steel tube, and wherein the first hydrostatic pressure differential sensor is configured to maintain air in the second stainless steel tube when the second end of the second stainless steel tube is inserted into the liquid contained in the vessel.

3. The sensor device of claim 2, wherein the sensor device comprises:
a second air injector for injecting air into the first end of the second stainless steel tube.

4. The sensor device of claim 1, wherein the sensor device comprises:
a second stainless steel tube; and
a second hydrostatic pressure differential sensor for maintaining air in the second stainless steel tube, wherein the first hydrostatic pressure differential sensor is configured to measure the volume of the liquid contained in the vessel according to a pressure measured by the second hydrostatic pressure differential sensor.

5. The sensor device of claim 1, wherein the first hydrostatic pressure differential sensor comprises two non-differential pressure sensors and a differentiator for providing the difference between the pressures measured by the two non-differential sensors.

6. The sensor device of claim 1, wherein the sensor device comprises:
a second stainless steel tube for protecting the second inlet of the first hydrostatic pressure differential sensor.

7. The sensor device of claim 1, wherein the first hydrostatic pressure differential sensor comprises an electronic data processor coupled to the air injector, and wherein the electronic data processor is configured to inject air into the first stainless steel tube before obtaining a measure by the first hydrostatic pressure differential sensor.

8. The sensor device of claim 1, wherein the second end of the first stainless steel tube is cut at angle that is greater than 30° and less than 60°.

9. The sensor device of claim 1, wherein the first end of the first stainless steel tube is coupled to the first hydrostatic pressure differential sensor.

10. The sensor device of claim 1, wherein the sensor device comprises:

a temperature sensor coupled to the first stainless steel tube for protecting the second inlet of the first hydrostatic pressure differential sensor, wherein the first hydrostatic pressure differential sensor is configured to measure the volume of the liquid contained in the vessel according to a temperature measure by the temperature sensor.

11. The sensor device of claim 1, wherein the sensor device comprises:
one or more sensors for measuring pH, turbidity, color, sugar and/or alcohol concentration of the liquid.

12. The sensor device of claim 1, wherein the first hydrostatic pressure differential sensor is configured to measure a density of the liquid contained in the vessel.

13. The sensor device of claim 1, wherein the sensor device is cylindrical, prismatic with a quadrangular section, prismatic with a rectangular section, or frusto-conical.

14. The sensor device of claim 1, wherein the sensor device comprises:
a wireless transmitter for transmitting data collected by the first hydrostatic pressure differential sensor.

15. The sensor device of claim 14, wherein the collected data are transmitted periodically.

16. The sensor device of claim 1, wherein the liquid is wine, sparkling wine, juice, or spirit drink.

17. The sensor device of claim 1, wherein the vessel is a barrel, tun, cask or vat.

18. The sensor device of claim 1, wherein the sensor device comprises a stopper of the vessel.

19. The sensor device of claim 1, wherein the sensor device comprises:
a processor configured to store data collected by the first hydrostatic pressure differential sensor.

20. The sensor device of claim 1, wherein the sensor device comprises:
a sound alarm that is operable according to data collected by the first hydrostatic pressure differential sensor.

21. The sensor device of claim 1, wherein the sensor device comprises:
a visual alarm that is operable according to data collected by the first hydrostatic pressure differential sensor.

22. The sensor device of claim 1, wherein the sensor device is wirelessly coupled to a remote alarm that is operable according to data collected by the first hydrostatic pressure differential sensor.

23. The sensor device of claim 1, wherein the sensor device comprises:
a second stainless steel tube comprising two ends, wherein a first end of the second stainless steel tube is coupled to an opening in a side of the first stainless steel tube, and wherein a second end of the second stainless steel tube is configured to be inserted into the liquid contained in the vessel.

24. The sensor device of claim 1, wherein the first hydrostatic pressure differential sensor is configurable to be calibrated when the second end of the first stainless steel tube is outside the liquid contained in the vessel.

25. The sensor device of claim 1, wherein the first hydrostatic pressure differential sensor is configurable to be calibrated when the second end of the first stainless steel tube is inserted into the liquid contained in the vessel, and wherein a depth of the second end of the first stainless steel tube is predetermined.

* * * * *